United States Patent [19]

Otake

[11] 4,337,173
[45] Jun. 29, 1982

[54] SOLID-SOLUTION TYPE CRYSTALLINE OXIDES AND THEIR PRECURSORS

[75] Inventor: Masayuki Otake, Yokohama, Japan

[73] Assignee: Mitsubishi Chemical Industries, Ltd., Tokyo, Japan

[21] Appl. No.: 189,346

[22] Filed: Sep. 22, 1980

[51] Int. Cl.³ .......................... B01J 27/14; C01B 15/16
[52] U.S. Cl. ..................................... 252/435; 252/437; 423/306
[58] Field of Search ................. 252/435, 437; 423/306

[56] References Cited

U.S. PATENT DOCUMENTS

| | | | |
|---|---|---|---|
| 3,832,359 | 8/1974 | Freerks et al. ................ | 260/346.8 A |
| 3,867,411 | 2/1975 | Raffelson et al. ............ | 260/346.8 A |
| 3,888,886 | 6/1975 | Young et al. ................. | 260/346.8 A |
| 4,017,521 | 4/1977 | Schneider .................... | 260/346.8 A |
| 4,080,312 | 3/1978 | Farha, Jr. et al. ............. | 252/435 X |
| 4,100,106 | 7/1978 | Stefani et al. ................ | 252/437 |
| 4,158,671 | 6/1979 | Barone ......................... | 252/437 X |

FOREIGN PATENT DOCUMENTS 45-34802 11/1970 Japan .
53-60391 5/1978 Japan .

OTHER PUBLICATIONS

Some selectivity criteria in Mild-Oxidation Catalysis Journal of Catalysts 57, 236-252 1979 Border et al.

Primary Examiner—Delbert E. Gantz
Assistant Examiner—William G. Wright
Attorney, Agent, or Firm—Kenway & Jenney

[57] ABSTRACT

A substitutional solid-solution type crystalline oxide represented by the general formula:

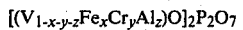

$$[(V_{1-x-y-z}Fe_xCr_yAl_z)O]_2P_2O_7$$

wherein $0 \leq x \leq 0.40$, $0 \leq y \leq 0.40$, $0 \leq z \leq 0.40$, and $0 < x+y+z \leq 0.40$, and having the same crystal structure as $(VO)_2P_2O_7$, and a precursory substitutional solid-solution type crystalline oxide therefor having a specific crystal structure. The former oxide has high activity and selectivity as a catalyst for vapor phase oxidation, particularly for producing maleic anhydride from a hydrocarbon containing four carbon atoms.

9 Claims, No Drawings

SOLID-SOLUTION TYPE CRYSTALLINE OXIDES AND THEIR PRECURSORS

BACKGROUND OF THE INVENTION

1. Field of the Invention

This invention relates to novel substitutional solid-solution type crystalline oxides which are useful as a catalyst for vapor phase oxidation, particularly for producing maleic anhydride from a hydrocarbon containing four carbon atoms, and novel precursory substitutional solid-solution type crystalline oxides therefor.

2. Description of the Prior Art

For the preparation of maleic anhydride by the vapor phase oxidation of a hydrocarbon containing four carbon atoms, there are known catalysts which are composed of vanadium-phosphorus composite oxides as disclosed, for example, in Japanese Patent Publication No. 39037/1978, and Japanese patent application Laid-Open Specification Nos. 63982/1973, 95990/1976, 156193/1977 and 146992/1978, and which are composed of oxides containing vanadium, phosphorus, and iron, chromium, or the like as disclosed, for example, in U.S. Pat. No. 3,156,705, Japanese Patent Publication Nos. 43928/1978 and 43929/1978, and Japanese patent application Laid-Open Specification Nos. 60391/1978 and 61587/1978. The former group of known catalysts are composed of crystalline oxides, while the latter catalysts are amorphous.

In order to improve the performance of the vanadium-phosphorus composite oxide catalyst in vapor phase oxidation, I have made an extensive study of the suitability for vapor phase oxidation of a catalyst composed of an oxide containing not only vanadium and phosphorus, but also a third component. As the result, I have discovered that the addition of iron and chromium is detrimental to a crystalline vanadium-phosphorus composite oxide, though it may be effective to some extent to incorporate them into an amorphous vanadium-phosphorus composite oxide, but that a novel substitutional solid-solution type crystalline oxide containing iron, chromium and/or aluminum substituted for a part of vanadium, while retaining the crystal structure, of vanadyl pyrophosphate shown as $(VO)_2P_2O_7$, provides high activity and selectivity as a catalyst for vapor phase oxidation. I have also discovered that a novel substitutional solid-solution type crystalline oxide containing iron, chromium and/or aluminum substituted for a part of vanadium in a crystalline vanadium-phosphorus oxide having a specific crystal structure, while retaining its crystal structure, provides a precursor of the aforementioned substitutional solid-solution type crystalline oxide.

SUMMARY OF THE INVENTION

It is, therefore, an object of this invention to provide a novel substitutional solid-solution type crystalline oxide which is useful as a catalyst for vapor phase oxidation.

It is another object of this invention to provide a novel vanadium-phosphorus composite oxide which forms a catalyst having high activity and selectivity in the reaction for preparing maleic anhydride from a hydrocarbon containing four carbon atoms.

It is a further object of this invention to provide a novel substitutional solid-solution type crystalline oxide serving as a precursor of a vanadium-phosphorus crystalline oxide which is useful as a catalyst for vapor phase oxidation.

Other objects and advantages of this invention will be set forth in the following description, or obvious therefrom to anybody of ordinary skill in the art.

The aforementioned objects and advantages of this invention will be attained by the substitutional solid-solution type crystalline oxides of this invention which are useful as a catalyst for vapor phase oxidation, or as a precursor thereof.

The crystalline oxide of this invention which is useful as a catalyst for vapor phase oxidation (hereinafter referred to as the "final crystalline oxide") includes a substitutional solid-solution type crystalline oxide which is represented by the general formula:

$$[(V_{1-x-y-z}Fe_xCr_yAl_z)O]_2P_2O_7$$

wherein $0 \leq x \leq 0.40$, $0 \leq y \leq 0.40$, $0 \leq z \leq 0.40$, and $0 < x+y+z \leq 0.40$, and having the same crystal structure as $(VO)_2P_2O_7$.

The crystalline oxide of this invention which is useful as a precursor (hereinafter referred to as the "precursory crystalline oxide") comprises a substitutional solid-solution type crystalline oxide which is composed of vanadium, phosphorus, oxygen, and at least one element selected from the group consisting of iron, chromium and aluminum, and which has the same crystal form as a crystalline oxide composed of vanadium, phosphorus and oxygen, and having the main peaks in the X-ray diffraction spectrum (using a Cu-Kα anticathode) at a diffraction angle (2θ) of 15.7°, 19.8°, 24.4°, 27.3°, 30.6° and 40.6°, and in which a part of vanadium is substituted by said at least one element.

DETAILED DESCRIPTION OF THE INVENTION

The aforementioned precursory crystalline oxide is a blue crystal composed of vanadium, phosphorus, oxygen, and at least one element selected from the group consisting of iron, chromium and aluminum which is substituted for a part of vanadium forming the crystal. The crystalline oxide, excluding oxygen, hydrogen and water of crystallization, is represented by the following formula:

$$V_{1.0-x-y-z}Fe_xCr_yAl_zP_{1.0}$$

wherein $0 \leq x \leq 0.40$, $0 \leq y \leq 0.40$, $0 \leq z \leq 0.40$, and $0.0005 \leq x+y+z \leq 0.40$.

The precursory crystalline oxides show substantially the same X-ray diffraction pattern as the vanadium-phosphorus crystalline oxide described in Japanese patent application Laid-Open Specification No. 95990/1976. The diffraction angle and intensity of its main diffraction peaks are as shown in Table 1 below, and a very slight shift in the lattice distance is observed with an increase in the degree of vanadium substitution.

TABLE 1

| Diffraction Angle (2θ) (Anticathode: Cu-Kα) | Intensity |
|---|---|
| 15.7° | High |
| 19.8° | Medium |
| 24.4° | Medium |
| 27.3° | Medium |
| 30.6° | Medium High |

TABLE 1-continued

| Diffraction Angle (2θ) (Anticathode: Cu-Kα) | Intensity |
|---|---|
| 40.6° | Low |

The vanadium compounds which may be used for preparing the precursory crystalline oxides include, for example, oxides, oxyacids and oxyhalides of pentavalent vanadium, such as vanadium pentoxide, metavanadic acid, pyrovanadic acid, and vanadium oxytrichloride, or oxychlorides of tetravalent vanadium, such as vanadium oxydichloride. Examples of the phosphorus compounds which can be used include oxides, oxyacids and oxyhalides of pentavalent phosphorus, such as phosphorus pentoxide, orthophosphoric acid, pyrophosphoric acid, tripolyphosphoric acid and phosphorus oxytrichloride. Iron, chromium and aluminum may be incorporated in the form of their respective halides, oxyacids, acetates, phosphates, or the like.

A precursory crystalline oxide may be prepared by dissolving the aforementioned starting compounds in water, and if a compound of pentavalent vanadium is used, adding a reducing agent such as hydrazine, hydroxylamine, or their hydrohalogenates, or a hydrogen halide, to form a homogeneous aqueous solution containing tetravalent vanadium, pentavalent phosphorus, a halogen ion, and iron, chromium and/or aluminum, and separating a crystal from the solution by concentration, evaporation to dryness, or otherwise. A crystal having a large specific surface area can be obtained if a hydrogen halide trapping agent, such as ethylene oxide or ethylene carbonate, is added into the aqueous solution to be concentrated. The quantity of each of the starting compounds is preferably controlled to ensure that phosphorus has an atomic ratio of 0.8 to 1.25, more preferably 1.00 to 1.10, to the total quantity of vanadium, and a third component consisting of iron, chromium and/or aluminum, and that the third component have an atomic ratio of 0.01 to 0.4, particularly 0.05 to 0.25, to the total quantity of vanadium and the third component. The initial concentration of phosphoric acid in the aqueous solution is controlled to 5 to 50% by weight, preferably 10 to 35% by weight.

A final crystalline oxide which is useful as a catalyst for vapor phase oxidation can be obtained if the precursory crystalline oxide prepared as hereinabove described is fired at a temperature of 300° C. to 750° C. in an inert gas such as nitrogen, or a gas for vapor phase oxidation containing a hydrocarbon and oxygen.

The final crystalline oxide thus obtained is a substitutional solid-solution type crystalline oxide of the structure having a part of vanadium in $(VO)_2P_2O_7$ replaced by iron, chromium and/or aluminum, and can be represented by the following general formula:

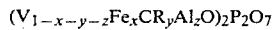
$(V_{1-x-y-z}Fe_xCR_yAl_z O)_2P_2O_7$ wherein $0 \leq x \leq 0.40$, $0 \leq y \leq 0.40$, $0 \leq z \leq 0.40$, and $0 < x+y+z \leq 0.40$. For a vapor phase oxidation catalyst, it is preferable to use a crystalline oxide of the formula in which x, y or z is in the range of 0.001 to 0.40, particularly 0.005 to 0.25.

The final crystalline oxide has a crystal structure equal to that of the compound $(VO)_2P_2O_7$, which is called the B-phase in Japanese Patent Publication No. 39037/1978, and discussed in detail in the Journal of Catalysis, 57, pages 236 to 252 (1979), and shows an X-ray diffraction pattern which is virtually identical to that of $(VO)_2P_2O_7$. Its diffraction peak, however, shows a tendency to shift, without any change in strength, due to a very slight variation in the lattice distance with an increase in the degree of vanadium substitution. It appears impossible to obtain a final crystalline oxide in which iron, chromium and/or aluminum is substituted for more than 40% of vanadium, however careful one may be in preparing it.

The final crystalline oxide may be either applied to a carrier, or molded by a customary method, for use as a catalyst for vapor phase oxidation in a fixed or fluidized bed. If desired, it is also possible to apply the precursory crystalline oxide to a carrier, or mold it into an appropriate shape by a customary method, and fire it at a temperature of 300° C. to 750° C. to accomplish both the conversion thereof into the final crystalline oxide and the formation of a catalyst simultaneously.

The invention will now be described more specifically with reference to examples, which are not limitative, but only illustrative of this invention.

EXAMPLE 1

(Precursory Crystalline Oxide)

11.529 g of 85% by weight orthophosphoric acid were dissolved in 70 g of water, and an aqueous solution obtained by dissolving 2.3625 g of hydrazine dihydrochloride in 30 g of water was added thereinto in a flask having a reflux condenser. 8.1855 g of vanadium pentoxide were added little by little into the flask over a bath of water at 75° C., while the contents of the flask were being stirred. The contents of the flask generated nitrogen and other gases for about half an hour with the progress of reduction of vanadium, and after they stopped bubbling almost completely, they were boiled under reflux for half an hour, whereby the reduction of vanadium was completed. After the contents of the flask were allowed to cool, 1.622 g of iron trichloride ($FeCl_3$) were added and dissolved in the contents of the flask, and they were boiled again for an hour under reflux. Then, the contents of the flask were transferred into an evaporating dish, were dried under stirring in a bath having a controlled temperature of 130° C. until the smell of hydrochloric acid ceased to be detected, and were allowed to stand for one night. About 50 ml of water were added to the deposit, and after the mixture was boiled, it was filtered, and the filter residue was washed with water, and dried, whereby a blue crystal was obtained.

The crystal thus obtained had an iron atomic ratio of 0.10, and a phosphorus atomic ratio of 1.0, relative to the total quantity of vanadium and iron therein. The analysis of the crystal by X-ray diffraction (using a Cu-Kα anticathode) indicated an X-ray diffraction pattern which coincided substantially with that set forth in Table 1. Table 2 below shows the lattice distances measured precisely with α-alumina as the internal standard substance ($\lambda = 1.54050$ Å) at the diffraction peaks at an angle 2θ of about 27.0° and 24.2°, respectively.

EXAMPLES 2 TO 4

(Precursory Crystalline Oxide)

Substitutional solid-solution type crystalline oxides having an iron atomic ratio of 0.05, 0.20 and 0.30, respectively, to the total quantity of vanadium and iron were prepared by repeating the procedures of Example 1, except that the quantities of vanadium pentoxide and iron trichloride were altered. Each of these oxides showed an X-ray diffraction pattern which was substantially identical both in diffraction angle and strength to that shown in Table 1, but the position of their diffraction lines had a tendency to shift slightly with an increase in the degree of substitution by iron for vanadium.

EXAMPLE 5

(Precursory Crystalline Oxide)

A substitutional solid-solution type crystalline oxide comprising a blue crystal having a chromium atomic ratio of 0.1 and a phosphorus atomic ratio of 1.0, to the total quantity of vanadium and chromium, was prepared by repeating the procedures of Example 1, except that 2.6645 g of chromium trichloride ($CrCl_3.6H_2O$) were used instead of iron trichloride. The analysis of the crystal by X-ray diffraction (using a Cu-K$\alpha$ anticathode) indicated a diffraction pattern which was substantially identical to that shown in Table 1. Table 2 shows the lattic distances measured precisely at the diffraction peaks at an angle $2\theta$ of about 27.0° and 24.2°, respectively, as set forth in Example 1.

EXAMPLE 6

(Precursory Crystalline Oxide)

A blue crystal having an Fe/Cr atomic ratio of 2, an (Fe+Cr)/(V+Fe+Cr) atomic ratio of 0.06 and a P/(V+Fe+Cr) atomic ratio of 1.0 was prepared by repeating the procedures of Example 1, except that the quantity of vanadium pentoxide was changed to 8.530 g, and that 0.6488 g of iron trichloride and 0.5329 g of chromium trichloride hexahydrate ($CrCl_3.6H_2O$) were used instead of 1.622 g of iron trichloride. The analysis of the crystal by X-ray diffraction (using a Cu-K$\alpha$ anticathode) indicated a diffraction pattern which was substantially identical to that shown in Table 1. Table 2 shows the lattice distances measured at the diffraction peaks at an angle $2\theta$ of about 27.0° and 24.2°, respectively, as set forth in Example 1.

EXAMPLE 7

(Precursory Crystalline Oxide)

A dark blue crystal having an Al/(V+Al) atomic ratio of 0.1 and a P/(V+Al) atomic ratio of 1.0 was prepared by repeating the procedures of Example 1, except that 1.328 g of aluminum trichloride ($AlCl_3$) were used instead of iron trichloride. The analysis of the crystal by X-ray diffraction (using a Cu-K$\alpha$ anticathode) indicated a diffraction pattern which was substantially identical to that shown in Table 1. Table 2 shows the lattice distances measured at the diffraction peaks at an angle of about 27.0° and 24.2°, respectively, as set forth in Example 1.

COMPARATIVE EXAMPLE 1

(Oxide Corresponding to a Precursory Crystalline Oxide)

11.529 g of 85% by weight orthophosphoric acid were added into 60 ml of water, and an aqueous solution obtained by dissolving 2.625 g of hydrazine dihydrochloride in 30 ml of water was added thereinto. The resulting aqueous solution was heated over a bath of water at 80° C., and after 9.095 g of vanadium pentoxide were added little by little into the solution while it was being stirred, the solution was kept in agitation for half an hour, and boiled under reflux for half an hour, whereby a blue aqueous solution was obtained. The aqueous solution thus obtained was dried by evaporation in a bath having a controlled temperature of 130° C. as set forth in Example 1, whereby a light blue crystal was obtained. The crystal thus obtained had a phosphorus/vanadium atomic ratio of 1.0, and showed an X-ray diffraction pattern coinciding with that shown in Table 1. Table 2 shows the lattice distances measured precisely at the diffraction peaks at an angle $2\theta$ of about 27.0° and 24.2°, respectively.

TABLE 2

| | Composition (Excluding oxygen) | Lattice Distance (Å) $2\theta$ = about 27.0° | Lattice Distance (Å) $2\theta$ = about 24.2° |
|---|---|---|---|
| Comparative Example 1 | $V_{1.0}P_{1.0}$ | 3.297 | 3.678 |
| Example 1 | $V_{0.90}Fe_{0.10}P_{1.0}$ | 3.293 | 3.674 |
| Example 5 | $V_{0.90}Cr_{0.10}P_{1.0}$ | 3.293 | 3.676 |
| Example 6 | $V_{0.94}Fe_{0.04}Cr_{0.02}P_{1.0}$ | 3.296 | 3.674 |
| Example 7 | $V_{0.90}Al_{0.10}P_{1.0}$ | 3.289 | 3.670 |

EXAMPLE 8

(Final Crystalline Oxide)

The precursory crystalline oxide obtained in Example 1 was fired at 550° C. for two hours in a stream of nitrogen, whereby there was formed a crystalline oxide shown as $(V_{0.9}Fe_{0.1})_2P_2O_7$. The analysis of the crystalline oxide by X-ray diffraction (using a Cu-K$\alpha$ anticathode) indicated a diffraction pattern which was identical to that of $(VO)_2P_2O_7$. As the position of the diffraction peak showed a slight shift from that of $(VO)_2P_2O_7$, the lattice distance on the (020) plane was precisely measured with $\alpha$-alumina as the internal standard substance. The results are shown in Table 5.

The crystalline oxide thus obtained was formed into pellets having a diameter of 7 mm and a thickness of 3 mm, and the pellets were crushed to form a catalyst having a particle size of 14 to 24 mesh (Japanese Industrial Standard). 0.5 ml of the catalyst thus obtained was placed in a glass microreactor having an inside diameter of 6 mm, and air containing 1.5% by volume of n-butane was caused to flow therethrough at a GHSV of 500 hr$^{-1}$, whereby the vapor phase oxidation of n-butane was carried out at an optimum reaction temperature. The gaseous reaction product was introduced directly into a gas chromatograph through a heat insulated gas sampler, analyzed, and measured. Table 6 shows the optimum reaction temperature, the rate of n-butane conversion, and the yield of maleic anhydride.

Table 4 shows the results obtained by repeating the reaction as hereinabove described, except for the GHSV of 2,000 hr$^{-1}$.

The aforementioned molded pellets were crushed to form a powder having a particle size of 8 to 14 mesh (Japanese Industrial Standard). 10 ml of this powder were placed in a glass reactor having an inside diameter of 25 mm, and air containing 1.5% by volume of 1-butene was caused to flow therethrough at a GHSV of 1,000 hr$^{-1}$, whereby the vapor phase oxidation of 1-butene was carried out at an optimum reaction temperature. The reaction product was absorbed in water, and analyzed by potentiometric titration and gas chromatography. The results are shown in Table 3.

COMPARATIVE EXAMPLE 2

(Oxide Corresponding to a Precursory Crystalline Oxide)

An oxide corresponding to a precursory crystalline oxide was prepared by repeating the procedures of Example 1, except that 9.095 g of vanadium pentoxide were used instead of 8.186 g, and that no iron trichloride was used. The oxide was fired as set forth in Example 8 to prepare a crystalline oxide shown as $(VO)_2P_2O_7$. The analysis of the crystalline oxide by X-ray diffraction (using a Cu-K$\alpha$ anticathode) gave the results coinciding with the data on $(VO)_2P_2O_7$ as set forth in Table 3 in the Journal of Catalysis, 57, page 240 (1979). Table 5 shows the lattice distance measured on the (020) plane of the crystalline oxide as set forth in Example 8. The crystalline oxide had a specific surface area of 12.2 m$^2$/g.

The procedures of Example 8 were repeated for preparing a catalyst from the crystalline oxide, and testing it for vapor phase oxidation of n-butane at a GHSV of 500 hr$^{-1}$ and 2,000 hr$^{-1}$, and 1-butene at a GHSV of 1,000 hr$^{-1}$. The results are shown in Tables 6, 4 and 3, respectively.

TABLE 3

(Examples of Vapor Phase Oxidation of 1-Butene)

| Catalyst | | Optimum Reaction Temp. (°C.) | Rate of 1-Butene Conversion (%) | Yield of Maleic Anhydride (%) |
|---|---|---|---|---|
| Example 8 | $(V_{0.9}Fe_{0.1}O)_2P_2O_7$ | 380 | 100 | 57.1 |
| Comparative Example 2 | $(VO)_2P_2O_7$ | 368 | 100 | 55.4 |

EXAMPLE 9

(Final Crystalline Oxide)

The precursory crystalline oxide obtained in Example 3 was fired as set forth in Example 8, whereby a crystalline oxide shown as $(V_{0.8}Fe_{0.2}O)_2P_2O_7$ was prepared. The crystalline oxide thus obtained showed an X-ray diffraction pattern coinciding substantially with that of $(VO)_2P_2O_7$, but a very slight shift in the position of the diffraction peak. A weak peak of the diffraction line for $\alpha$-quartz type ferric phosphate (as identified by the ASTM card) indicated the presence of a very small amount of ferric phosphate as impure matter.

The procedures of Example 8 were repeated for preparing a catalyst from the crystalline oxide, and testing it for vapor phase oxidation of n-butane at a GHSV of 500 hr$^{-1}$ and 2,000 hr$^{-1}$. The results are shown in Tables 6 and 4, respectively.

TABLE 4

(Examples of Vapor Phase Oxidation of n-Butane at a GHSV of 2,000 hr$^{-1}$)

| Catalyst | | Optimum Reaction Temp. (°C.) | Rate of n-Butane Conversion (%) | Yield of Maleic Anhydride (%) |
|---|---|---|---|---|
| Comparative Example 2 | $(VO)_2P_2O_7$ | 480 | 93.0 | 59.3 |
| Example 8 | $(V_{0.9}Fe_{0.1}O)_2P_2O_7$ | 475 | 91.8 | 63.7 |
| Example 9 | $(V_{0.8}Fe_{0.2}O)_2P_2O_7$ | 462 | 95.2 | 59.0 |

EXAMPLE 10

(Final Crystalline Oxide)

The precursory crystalline oxide obtained in Example 2 was fired as set forth in Example 8, whereby a crystalline oxide shown as $(V_{0.95}Fe_{0.05}O)_2P_2O_7$ was prepared. The crystalline oxide thus obtained showed an X-ray diffraction pattern coinciding with that of $(VO)_2P_2O_7$. Table 5 shows the lattice distance measured precisely on the (020) plane as set forth in Example 8. The crystalline oxide had a specific surface area of 9.3 m$^2$/g.

The procedures of Example 8 were repeated for preparing a catalyst from the crystalline oxide, and testing it for vapor phase oxidation of n-butane at a GHSV of 500 hr$^{-1}$. The results are shown in Table 6.

EXAMPLE 11

(Final Crystalline Oxide)

The precursory crystalline oxide obtained in Example 4 was fired as set forth in Example 8, whereby a crystalline oxide shown as $(V_{0.7}Fe_{0.3}O)_2P_2O_7$ was prepared. The crystalline oxide thus obtained showed an X-ray diffraction pattern which was substantially identical to that of the oxide obtained in Example 9.

The procedures of Example 8 were repeated for preparing a catalyst from the crystalline oxide, and testing it for vapor phase oxidation of n-butane at GHSV of 500 hr$^{-1}$. The results are shown in Table 6.

EXAMPLE 12

(Final Crystalline Oxide)

The precursory crystalline oxide obtained in Example 6 was fired as set forth in Example 8, whereby a crystalline oxide shown as $(V_{0.94}Fe_{0.04}Cr_{0.02}O)_2P_2O_7$ was prepared. The crystalline oxide thus obtained had a specific surface area of 18.1 m$^2$/g, and showed an X-ray diffraction pattern coinciding substantially with that of $(VO)_2P_2O_7$. Table 5 shows the lattice distance measured precisely on the (020) plane as set forth in Example 8.

The procedures of Example 8 were repeated for preparing a catalyst from the crystalline oxide, and testing it for vapor phase oxidation of n-butane at a GHSV of 500 hr$^{-1}$. The results are shown in Table 6.

TABLE 5

[Lattice Distance on the (020) Plane]

| | Composition of Crystalline Oxide | Lattice Distance (Å) |
|---|---|---|
| Comparative Example 2 | $(VO)_2P_2O_7$ | 3.867 |
| Example 10 | $(V_{0.95}Fe_{0.05}O)_2P_2O_7$ | 3.870 |
| Example 8 | $(V_{0.9}Fe_{0.1}O)_2P_2O_7$ | 3.874 |
| Example 12 | $(V_{0.94}Fe_{0.04}Cr_{0.02}O)_2P_2O_7$ | 3.872 |

COMPARATIVE EXAMPLE 3

7.74 g of the precursory blue crystal prepared in Comparative Example 2, and forming $(VO)_2P_2O_7$ if fired at 550° C., and 1.11 g of ferric phosphate tetrahydrate $(FePO_4 \cdot 4H_2O)$ were mixed together in the form of powder in a mortar. The mixture was fired at 550° C. for two hours in a stream of nitrogen, whereby a fired product having a phosphorus/vanadium/iron atomic ratio of 1.0:0.9:0.1 was obtained. The fired product showed clear X-ray diffraction peaks which were due to $(VO)_2P_2O_7$, and ferric phosphate, respectively.

The procedures of Example 8 were repeated for preparing a catalyst from the fired product, and testing it for vapor phase oxidation of n-butane at a GHSV of 500 hr$^{-1}$. The results are shown in Table 6.

EXAMPLE 13

(Final Crystalline Oxide)

A precursory crystalline oxide was prepared by repeating the procedures of Example 1, except that 1.352 g of iron trichloride hexahydrate and 0.6702 g of aluminum trichloride were used instead of 1.622 g of iron trichloride. The precursory crystalline oxide thus prepared was fired as set forth in Example 8, whereby there was formed a crystalline oxide having an X-ray diffraction pattern coinciding substantially with that of the crystalline oxide obtained in Example 8, and shown as $(V_{0.9}Fe_{0.05}Al_{0.05}O)_2P_2O_7$. The crystalline oxide thus obtained was tested for vapor phase oxidation of n-butane at a GHSV of 500 hr$^{-1}$ as set forth in Example 8. The results are shown in Table 6.

EXAMPLE 14

(Final Crystalline Oxide)

The precursory crystalline oxide obtained in Example 5 was fired as set forth in Example 8, whereby a crystalline oxide shown as $(V_{0.90}Cr_{0.10}O)_2P_2O_7$ was prepared. The analysis of the crystalline oxide by X-ray diffraction showed substantially the same results as those obtained in Example 8.

The procedures of Example 8 were repeated for preparing a catalyst from the crystalline oxide, and testing it for vapor phase oxidation of n-butane at a GHSV of 500 hr$^{-1}$. The results are shown in Table 6.

Example 15

(Final Crystalline Oxide)

The precursory crystalline oxide obtained in Example 7 was fired as set forth in Example 8, whereby a crystalline oxide shown as $(V_{0.90}Al_{0.10}O)_2P_2O_7$ was prepared. The analysis of the crystalline oxide by X-ray diffraction showed substantially the same results as those obtained in Example 8.

The procedures of Example 8 were repeated for preparing a catalyst from the crystalline oxide, and testing it for vapor phase oxidation of n-butane at a GHSV of 500 hr$^{-1}$. The results are shown in Table 6.

TABLE 6

(Examples of Vapor Phase Oxidation of n-Butane at a GHSV of 500 hr$^{-1}$)

| | Catalyst (Atomic Ratio) | Optimum Reaction Temp.(°C.) | Rate of n-Butane Converrsion(%) | Yield of Maleic Anhydride(%) |
|---|---|---|---|---|
| Comparative Example 2 | $V_{1.0}P_{1.0}$ | 418 | 95.0 | 70.6 |
| Example 10 | $V_{0.95}$ $Fe_{0.05}$ $P_{1.0}$ | 413 | 97.0 | 74.7 |
| Example 8 | $V_{0.9}$ $Fe_{0.1}$ $P_{1.0}$ | 380 | 95.4 | 75.8 |
| Example 9 | $V_{0.8}$ $Fe_{0.2}$ $P_{1.0}$ | 398 | 96.4 | 69.9 |
| Example 11 | $V_{0.7}$ $Fe_{0.3}$ $P_{1.0}$ | 380 | 89.1 | 64.1 |
| Example 12 | $V_{0.94}$ $Fe_{0.04}$ $Cr_{0.02}$ $P_{1.0}$ | 364 | 95.4 | 69.0 |
| Example 13 | $V_{0.9}$ $Fe_{0.05}$ $Al_{0.05}$ $P_{1.0}$ | 424 | 96.5 | 69.5 |
| Comparative Example 3 | $V_{0.9}$ $Fe_{0.1}$ $P_{1.0}$ | 370 | 90.4 | 63.6 |
| Example 14 | $V_{0.9}$ $Cr_{0.1}$ $P_{1.0}$ | 365 | 94.0 | 70.0 |
| Example 15 | $V_{0.9}$ $Al_{0.1}$ $P_{1.0}$ | 440 | 96.5 | 71.3 |

What is claimed is:

1. A process for preparing a crystalline oxide comprising:
    dissolving a pentavalent vanadium compound, a pentavalent phosphorus compound, a compound of at least one element selected from the group consisting of iron, chromium and aluminum, and hydrazine hydrochloride in water to form a homogeneous aqueous solution containing tetravalent vanadium, pentavalent phosphorus, chloride ion and said one element in relative amounts providing an atomic ratio of 0.8 to 1.25 for phosphorus to the total quantity of vanadium, iron, chromium and aluminum, and an atomic ratio of 0.01 to 0.4 for the total quantity of iron, chromium and aluminum to the total quantity of vanadium, iron, chromium and aluminum, and
    concentrating and evaporating the solution to dryness to provide a solid-solution type crystalline oxide precursor of vanadium phosphorus, oxygen and said one element having an X-ray diffraction spectrum (Cu-Kα anticathode) with main peaks at diffraction angles (2θ) of 15.7°, 19.8°, 24.4°, 27.3°, 30.6°, and 40.6°.

2. A process in accordance with claim 1 wherein the atomic ratio of phosphorus to the total quantity of vanadium, iron, chromium and aluminum is 1.00 to 1.10 and the atomic ratio of the total quantity of iron, chromium and aluminum to the total quantity of vanadium, iron, chromium and aluminum is 0.05 to 0.25.

3. A process in accordance with claim 1 or 2 wherein the initial concentration of phosphoric acid in said aqueous solution is 5 to 50% by weight.

4. A process in accordance with claim 3 wherein said initial concentration is 10 to 35% by weight.

5. A process in accordance with claim 1 further comprising:
    heating said crystalline oxide precursor at a temperature of 300° to 750° C. to obtain a solid-solution type crystalline oxide catalyst of the formula:

$$[(V_{1-x-y-z}Fe_xCr_yAl_z)O]_2P_2O_7$$

wherein $0 \leq x \leq 0.40$, $0 \leq y \leq 0.40$, $0 \leq z \leq 0.40$, and $0 < x+y+z \leq 0.40$, and having the same crystal structure as $(VO)_2P_2O_7$.

6. A process in accordance with claim 5 wherein said heating of said precursor is in an inert gas.

7. A process in accordance with claim 5 wherein said heating is a vapor phase oxidation in an atmosphere containing a hydrocarbon and oxygen.

8. The catalyst precursor obtained by the process of claim 1 or 2.

9. The catalyst obtained by the process of claim 5.

* * * * *

UNITED STATES PATENT AND TRADEMARK OFFICE
CERTIFICATE OF CORRECTION

PATENT NO. : 4,337,173

DATED : June 29, 1982

INVENTOR(S) : Masayuki Otake

It is certified that error appears in the above—identified patent and that said Letters Patent is hereby corrected as shown below:

On the title page add the following:

---[30] Foreign Application Priority Data

Oct. 26, 1979  JAPAN  138431/1979
    Nov. 7, 1979   JAPAN  143964/1979---.

Col. 2, line 50 "0.0005" should be ---0.005---.

Col. 3, line 28 "separ■ting" should be ---separating---;

line 29, "crysta■" should be ---crystal---;

line 39, "particularly" should be ---more preferably---; and line 55 "CR" should be ---Cr---.

Col. 5, line 21 "lattic" should be ---lattice---.

UNITED STATES PATENT AND TRADEMARK OFFICE
CERTIFICATE OF CORRECTION

PATENT NO. : 4,337,173

DATED : June 29, 1982

INVENTOR(S) : Masayuki Otake

It is certified that error appears in the above—identified patent and that said Letters Patent is hereby corrected as shown below:

Col. 7, line 42 "$(V_{0.8}Fe_{0.2}O_2)_2P_2O_7$" should be ---$(V_{0.8}Fe_{0.2}O)_2P_2O_7$---.

Col. 9, 3rd subheading in Table 6, "converrsion" should be ---conversion---.

Col. 10, 3rd subheading in Table 6, "converrsion" should be ---conversion---.

Signed and Sealed this

Seventh Day of September 1982

[SEAL]

Attest:

Attesting Officer

GERALD J. MOSSINGHOFF

Commissioner of Patents and Trademarks